United States Patent [19]
Kuratle, III

[11] 3,989,501
[45] Nov. 2, 1976

[54] METHODS FOR INCREASING RICE CROP YIELDS

[75] Inventor: Henry Kuratle, III, Wilmington, Del.

[73] Assignee: E. I. Du Pont de Nemours and Company, Wilmington, Del.

[22] Filed: Mar. 6, 1975

[21] Appl. No.: 555,997

[52] U.S. Cl. .................................. 71/77; 71/88; 71/93; 71/DIG. 1; 47/57.6
[51] Int. Cl.$^2$ .................................. A01N 21/02
[58] Field of Search .................... 71/93, 88, 77

[56] References Cited
UNITED STATES PATENTS
3,855,219  12/1974  Fuchs et al. ............... 260/248 NS
3,901,682  8/1975  Long II ............................. 71/93

OTHER PUBLICATIONS

Long, I "Altering Plant Flowering and Sexual, etc., " (1973), CA81, No. 34567c, (1974).

*Primary Examiner*—Glennon H. Hollrah

[57] ABSTRACT

A method for increasing the yield of rice crops involving application of an s-triazinedione such as 3-(4-chlorophenyl)-6-methoxy-s-triazine-2,4(1H,3H)-dione to the seed, seedlings, or soil in which the seed or seedlings are planted.

19 Claims, No Drawings

METHODS FOR INCREASING RICE CROP YIELDS

BACKGROUND OF THE INVENTION

Certain s-triazines have been found to enhance nitrogen uptake and metabolism and thereby increase grain yields under some circumstances (see, for example, C. J. Schweizer and S. K. Ries, Science 165, 73–75 (1967).

The s-triazinediones used in this invention and their use as herbicides are disclosed and claimed in copending U.S. Pat. application Ser. No. 301,853, filed Oct. 30, 1972, by Fuchs and Lin, now U.S. Pat. No. 3,855,219 (which is a continuation-in-part of U.S. Pat. application Ser. No. 268,767, filed July 3, 1972, which is in turn a continuation-in-part of U.S. Pat. application Ser. No. 181,202, filed Sept. 16, 1971, both now abandoned). The use of these compounds in a method for altering plant flowering and sexual reproduction is disclosed and claimed in copending U.S. Pat. application Ser. No. 301,852, filed Oct. 30, 1972, by Fitzgerald and Long, now U.S. Pat. No. 3,898,073. Finally, the use of these compounds in a method for increasing crop yields is disclosed and claimed in copending U.S. Pat. application Ser. No. 446,801, filed Feb. 28, 1974, by James D. Long, now U.S. Pat. No. 3,901,682 (which is a continuation-in-part of U.S. Pat. application Ser. No. 414,878, filed Oct. 12, 1973, which is in turn a continuation-in-part of U.S. Pat. application Ser. No. 348,320, filed Apr. 5, 1973, both now abandoned).

In particular, in U.S. Ser. No. 446,801, there is claimed a method for increasing the yield of wheat, rye, and corn crops comprising applying certain s-triazinediones to the crop plant during inflorescence initiation or early development.

It has now been discovered that rice crop yields can be significantly increased by applying certain of these s-triazinediones to rice seed, to rice seedlings, or to the soil into which these seeds or seedlings have been or will be placed.

SUMMARY OF THE INVENTION

This invention is a method of increasing the yield of rice crops which comprises applying an s-triazinedione to rice seed prior to planting, to rice seedlings prior to, during, or shortly after planting, or to the soil in which rice seeds or seedlings have been planted, are being planted, or will be planted, the s-triazinedione being a compound of the formula:

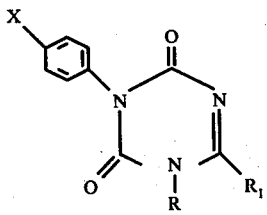

I wherein X is chlorine, bromine, or iodine;
R is hydrogen or a cation selected from lithium, sodium, potassium, calcium, magnesium, barium, or

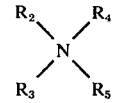

where
$R_2$, $R_3$, and $R_4$ can be the same or different and each can be hydrogen, alkyl of 1 through 4 carbon atoms, or hydroxy alkyl of 2 through 4 carbon atoms; and $R_5$ is hydrogen, alkyl of 1 through 12 carbon atoms, or benzyl; $R_2$ and $R_3$ can be taken together to form a ring that is -(CH$_2$)$_2$-O-(CH$_2$)$_2$- or -(CH$_2$)$_n$- where $n$ is 4–6 and $R_4$ and $R_5$ are H; and $R_1$ is SR$_6$ or OR$_6$ where $R_6$ is methyl or ethyl.

In particular, this invention is a method for increasing the yield of rice crops which comprises applying an s-triazinedione of formula I to rice seed or seedlings by any one or more of the following mechanisms:

a. applying the s-triazinedione to rice seed by seed soaking prior to planting;
b. applying the s-triazinedione to rice seed by seed treatment, such as seed coating or pelletization, prior to planting;
c. applying the s-triazinedione to rice seedlings by dipping prior to transplanting;
d. applying the s-triazinedione to rice seedlings as a foliar spray at any time from emergence until 80 days after planting; or
e. applying the s-triazinedione to rice seeds or seedlings as a soil application or a soil soak treatment, such as during rice field irrigation, shortly before planting, during planting, or at any time thereafter until 80 days after planting.

In addition, this invention comprises the intermediate product produced by the methods (a) and (b), above, i.e., soaked seed and treated (e.g., coated or pelletized) seed.

DETAILED DESCRIPTION OF THE INVENTION

Preferred Compounds

Certain of the compounds of formula I are preferred because of their higher activity and their ease of synthesis. These include 3-(4-chlorophenyl)-6-methoxy-s-triazine-2,4(1H,3H)-dione and salts thereof.

Synthesis of the Compounds

The compounds of formula I can be prepared by the process illustrated by the following equations:

1) $H_2N-\underset{R_1}{C}=NH + Cl-\underset{O}{\overset{O}{C}}-O-CH_3 \xrightarrow{NaOH} H_2N-\underset{R_1}{C}=N-\underset{O}{\overset{O}{C}}-O-CH_3$ 2) 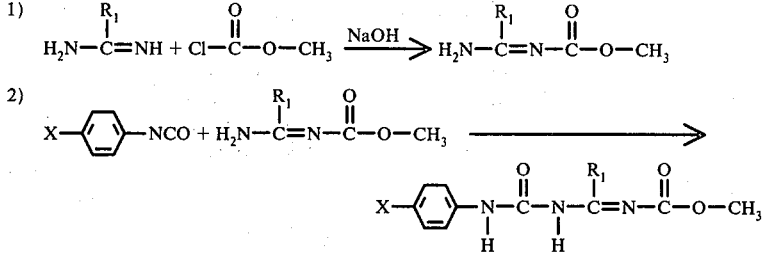

3)

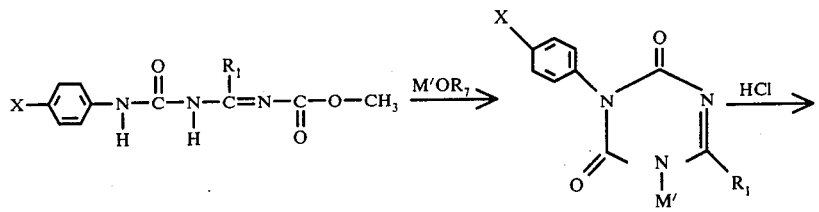

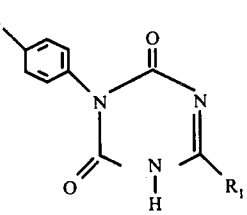

4)

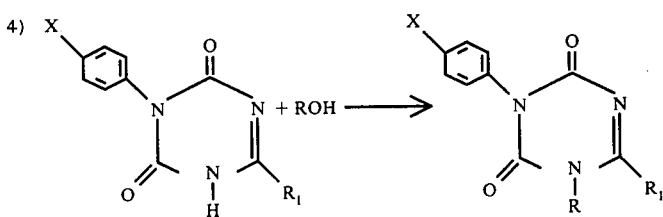

where
R and $R_1$ are as previously defined;
M' is an alkali metal; and
$R_7$ is hydrogen or alkyl of 1 through 4 carbon atoms.

The reaction products of equation 2) can be obtained by reacting the pseudourea or thiopseudourea first with a chloroformate as in equation 1), and then reacting the reaction products of equation 1) with an isocyanate as in equation 2). See, e.g., U.S. Pat. No. 3,855,219, granted Dec. 17, 1974, to Julius J. Fuchs and Kang Lin, pertinent subject matter of which is hereby incorporated by reference.)

The reaction products of equation 2) are then refluxed for a short time with an alkali metal alkoxide or hydroxide such as sodium or potassium methoxide or hydroxide in methanol to effect cyclization [equation 3)]. The solvent is evaporated under vacuum; the residue is (a) washed with ether or (b) dissolved in water and acidified. Acidification [method (b)] of the aqueous solution usually precipitates the desired s-triazinedione as an essentially pure solid. If the desired compound does not precipitate upon acidification, it is extracted into methylene chloride. The solvent is then evaporated and the dried residue is recrystallized. The essentially pure alkali metal or alkaline earth metal salt of the s-triazinedione (corresponding to the alkali metal or alkaline earth metal in the alkoxide or hydroxide) is obtained by washing the residue with ether and filtering the resulting solid [method (a)]. The same alkali metal and alkaline earth metal salts (where R=Li, Na, K, Ca, Mg, Ba) are also obtained by dissolving the s-triazinediones in methanol containing one equivalent of alkali metal or alkaline earth metal alkoxide or hydroxide such as sodium methoxide or hydroxide followed by evaporation of methanol.

Other salts (where $R=NR_2R_3R_4R_5$) of the s-triazinediones can be prepared similarly by dissolving the s-triazinediones (R=H) in an appropriate solvent such as water or methanol, adding one equivalent of the appropriate amine or ammonium hydroxide, and evaporating the solvent.

The following examples illustrate the processes described above. All parts are by weight unless otherwise indicated.

EXAMPLE 1

3-(4-Chlorophenyl)-6-methylthio-s-triazine-2,4(1H,3H)-dione

To a solution of 69.5 parts of 2-methyl-2-thiopseudourea sulfate and 47 parts of methyl chloroformate in 1,000 parts of water at 0° C. is added dropwise 56.9 parts of potassium hydroxide in 200 parts of water. The reaction mixture is stirred at room temperature for 3 hours and then extracted with methylene chloride. The methylene chloride extract is dried and the solvent evaporated at reduced pressure to give 45 g. of methyl N-(1-amino-1-methylthiomethylene)carbamate melting at 72°–77° C.

To a solution of 148 parts of said methyl N-(1-amino-1-methylthiomethylene)carbamate in 2,000 parts methylene chloride is added 154 parts of 4-chlorophenyl isocyanate. The reaction is stirred overnight. Then to it is added 54 parts of sodium methoxide in 540 parts of methanol. The reaction mixture is then refluxed for one hour. The reaction mass is cooled, and 2,000 parts of ether are added. The solid collected by filtration is dissolved in water and the solution neutralized with hydrochloric acid. The new solid thus formed is collected, dried, and recrystallized from ethanol/$H_2O$ to give 140 parts of 3-(4-chlorophenyl)-6-methylthio-s-triazine-2,4-(1H,3H)-dione melting at 292°–295° C.

EXAMPLE 2

3-(4-Chlorophenyl)-6-methoxy-s-triazine-2,4(1H,3H)-dione

To 52 parts of 2-methylpseudourea hydrogen sulfate in 250 parts of water at 0°–5° C. is added 31 parts of methyl chloroformate followed by dropwise addition of 74 parts of 50% sodium hydroxide. The reaction mass is stirred at room temperature for 3 hours and then extracted with methylene chloride. The methylene chloride extract is dried and the solvent evaporated. The residue is triturated with hexane to give 23 parts of methyl N-(1-amino-1-methoxymethylene)carbamate melting at 36°–39.5° C.

To 13 parts of the compound prepared above in 200 ml. of methylene chloride is added 15 parts of 4-chlorophenyl isocyanate. The reaction mass is stirred overnight. The solvent is evaporated and the residue refluxed overnight in 100 parts of 10% sodium methoxide in methanol. Water is added and the solution neutralized with hydrochloric acid. The crude solid collected by filtration is recrystallized from acetonitrile to give 7 parts of 3-(4-chlorophenyl)-6-methoxy-s-triazine-2,4(1H,3H)-dione melting at 238°–241° C.

EXAMPLE 3

The following s-triazinediones can be prepared by the procedure of Example 1 by substituting the listed 2-substituted thiopseudoureas and pseudoureas, for 2-methyl-2-thiopseudourea and by replacing p-chlorophenyl isocyanate with various isocyanates or isothiocyanates.

| Thiopseudourea or Pseudourea | Isocyanate or Isothiocyanate | s-Triazinediones |
|---|---|---|
| 2-ethylpseudourea | 4-chlorophenyl isocyanate | 3-(4-chlorophenyl)-6-ethoxy-s-triazine-2,4(1H,3H)-dione, m.p. 241–242° |
| 2-methylpseudourea | 4-bromophenyl isocyanate | 3-(4-bromophenyl)-6-methoxy-s-triazine-2,4(1H,3H)-dione, m.p. 208–210° |
| 2-methyl-2-thiopseudourea | 4-iodophenyl isocyanate | 3-(4-iodophenyl)-6-methylthio-s-triazine-2,4(1H,3H)-dione |
| 2-ethyl-2-thiopseudourea | 4-chlorophenyl isocyanate | 3-(4-chlorophenyl)-6-ethylthio-s-triazine-2,4(1H,3H)-dione |
| 2-ethyl-2-thiopseudourea | 4-bromophenyl isocyanate | 3-(4-bromophenyl)-6-ethylthio-s-triazine-2,4(1H,3H)-dione |
| 2-ethyl-2-thiopseudourea | 4-iodophenyl isocyanate | 3-(4-iodophenyl)-6-ethylthio-s-triazine-2,4(1H,3H)-dione |
| 2-methyl-2-thiopseudourea | 4-bromophenyl isocyanate | 3-(4-bromophenyl)-6-methylthio-s-triazine-2,4(1H,3H)-dione, m.p. 272–273° |
| 2-ethylpseudourea | 4-bromophenyl isocyanate | 3-(4-bromophenyl)-6-ethoxy-s-triazine-2,4(1H,3H)-dione |
| 2-ethylpseudourea | 4-iodophenyl isocyanate | 3-(4-iodophenyl)-6-ethoxy-s-triazine-2,4(1H,3H)-dione |
| 2-methylpseudourea | 4-iodophenyl isocyanate | 3-(4-iodophenyl)-6-methoxy-s-triazine-2,4(1H,3H)-dione |

EXAMPLE 4

Ammonium 3-(4-chlorophenyl)-6-methoxy-s-triazine-2,4(1H,3H)-dione

To a mixture of 10 parts of 3-(4-chlorophenyl)-6-methoxy-s-triazine-2,4(1H,3H)-dione and 100 parts of methanol is added one part of ammonia gas at 20° C. The solution is stirred for 30 minutes and then evaporated under vacuum to give 10.6 parts of ammonium 3-(4-chlorophenyl)-6-methoxy-s-triazine-2,4(1H,3H)-dione.

Similarly, the following s-triazinedione amine salts can be prepared by using the appropriate starting materials.

| | |
|---|---|
| methylammonium | 3-(4-chlorophenyl)-6-methoxy-s-triazine-2,4(1H,3H)-dione |
| tri-(2-hydroxyethyl)ammonium | 3-(4-chlorophenyl)-6-methoxy-s-triazine-2,4(1H,3H)-dione |
| dimethylammonium | 3-(4-chlorophenyl)-6-methoxy-s-triazine-2,4(1H,3H)-dione |
| ethylammonium | 3-(4-chlorophenyl)-6-methoxy-s-triazine-2,4(1H,3H)-dione |
| morpholinium | 3-(4-chlorophenyl)-6-methoxy-s-triazine-2,4(1H,3H)-dione |
| piperidinium | 3-(4-chlorophenyl)-6-methoxy-s-triazine-2,4(1H,3H)-dione |
| butylammonium | 3-(4-chlorophenyl)-6-methylthio-s-triazine-2,4(1H,3H)-dione |
| di-sec-butylammonium | 3-(4-chlorophenyl)-6-methylthio-s-triazine-2,4(1H,3H)-dione |
| diethylammonium | 3-(4-chlorophenyl)-6-methylthio-s-triazine-2,4(1H,3H)-dione |
| propylammonium | 3-(4-chlorophenyl)-6-methylthio-s-triazine-2,4(1H,3H)-dione |
| hexahydroazepidinium | 3-(4-chlorophenyl)-6-methylthio-s-triazine-2,4(1H,3H)-dione |
| pyrrolidinium | 3-(4-chlorophenyl)-6-methylthio-s-triazine-2,4(1H,3H)-dione |
| tetraethylammonium | 3-(4-chlorophenyl)-6-methylthio-s-triazine-2,4(1H,3H)-dione |
| trimethylammonium | 3-(4-chlorophenyl)-6-methoxy-s-triazine-2,4(1H,3H)-dione |
| tetramethylammonium | 3-(4-chlorophenyl)-6-methoxy-s-triazine-2,4(1H,3H)-dione |
| dodecyltrimethylammonium | 3-(4-chlorophenyl)-6-methoxy-s-triazine-2,4(1H,3H)-dione |
| 2-hydroxyethylammonium | 3-(4-chlorophenyl)-6-methoxy-s-triazine-2,4(1H,3H)-dione |
| benzylammonium | 3-(4-chlorophenyl)-6-methoxy-s-triazine-2,4(1H,3H)-dione |
| benzyltrimethylammonium | 3-(4-chlorophenyl)-6-methoxy-s-triazine-2,4(1H,3H)-dione |
| triethylammonium | 3-(4-chlorophenyl)-6-methoxy-s-triazine-2,4(1H,3H)-dione |
| 4-hydroxybutylammonium | 3-(4-chlorophenyl)-6-methoxy-s-triazine-2,4(1H,3H)-dione |

EXAMPLE 5

Sodium 3-(4-chlorophenyl)-6-methylthio-s-triazine-2,4-1H,3H)-dione

To a solution of 1.6 parts of sodium methoxide in 20 parts of methanol is added 8.0 parts of 3-(4-chlorophenyl)-6-methylthio-s-triazine-2,4(1H,3H)-dione. The solution is evaporated under vacuum and the white solid is triturated with methylene chloride and filtered to give sodium 3-(4-chlorophenyl)-6-methylthio-s-triazine-2,4(1H,3H)-dione.

Similarly, the following s-triazinedione salts can be prepared by using the appropriate starting materials.

| | |
|---|---|
| lithium | 3-(4-bromophenyl)-6-methylthio-s-triazine-2,4(1H,3H)-dione |
| potassium | 3-(4-bromophenyl)-6-methylthio-s-triazine-2,4(1H,3H)-dione |
| calcium | bis-3-(4-iodophenyl)-6-methylthio-s-triazine-2,4(1H,3H)-dione |
| magnesium | bis-3-(4-iodophenyl)-6-methylthio-s-triazine-2,4(1H,3H)-dione |
| barium | bis-3-(4-chlorophenyl)-6-methylthio-s-triazine-2,4(1H,3H)-dione |

Use of the Compounds

The compounds of formula I can be used to increase the yield of rice, one of the most important food crops of the world. Treatment of the rice seed or the young plants (via soil application or foliar spray) results in more grain produced per unit area. The rate of treatment will vary depending on the compound, method of application, time of application, and soil type (soil application).

In the case of seed soaking, soaking duration can range from ¼ to 24 hours. A soaking period of ½ to 12 hours is preferred, with 1–6 hours being most preferred. The aqueous seed soaking solution should contain 1,000–15,000 p.p.m. of a compound of formula I; 4,000–10,000 p.p.m. is preferred.

In the case of seed treatment, the compound can be applied as a solid seed coating, thus creating pelleted seed, or as a dust coating on the surface of the seed. The seeds are treated with 30–3,000 grams of a compound of formula I per 100 kg of seed; 60–1,250 grams per 100 kg of seed is preferred with 125–500 grams per 100 kg of seed most preferred.

The following experiment demonstrates the ability of the compounds used in the method of the present invention, and in particular, the ability of 3-(4-chlorophenyl)-6-methoxy-s-triazine-2,4(1H,3H)-dione, triethanolamine salt to increase the yield of rice plants by application of this compound to the seed prior to planting.

Rice seeds (cultivar, Starbonnet) were soaked for 6 hours in aqueous solutions of 3-(4-chlorophenyl)-6-methoxy-s-triazine-2,4(1H,3H)-dione, triethanolamine salt. Treated seeds were planted approximately 1.2 cm deep in Fallsington sandy loam soil contained in plastic pots 15 cm in diameter and then placed in the greenhouse. Eight days after planting each pot was thinned to ten plants. 173 Days after planting the plants were harvested, and the data following in Table I obtained:

TABLE I

| Treatment[a] | No seeds per pot | % of Control | Seed wt. gm per pot | % of Control |
|---|---|---|---|---|
| 3-(4-chlorophenyl)-6-methoxy-s-triazine-2,4(1H,3H)-dione, triethanolamine salt | | | | |
| 1000 ppm | 520 | 140 | 10.8 | 148 |
| 4000 | 664 | 179 | 13.6 | 186 |
| Control | 372 | | 7.3 | |

[a]Treatments were replicated four times. Data are averages of the four replications.

In the case of transplant dipping the concentration of the compounds of formula I in the dip solution can be 1,000–15,000 ppm with 4,000–10,000 ppm preferred. Dipping time can be ¼ to 24 hours; a dipping time of ½ to 12 hours is preferred with 1–6 hours most preferred.

Finally, in the case of both foliar spray and soil application, the compounds of formula I are applied to the rice foliage or to the soil in which the rice is planted at application rates from ¼ to 6 kg/ha; ½ to 4 kg/ha is preferred, and 1–3 kg/ha is most preferred. Application time may range from planting, or shortly before, to 80 days thereafter. It is preferred to apply the compound prior to 65 days after planting with the most preferred time of application being 10–45 days after planting.

The following experiment demonstrates the ability of the compounds used in the method of the present invention and, in particular, the ability of 3-(4-chlorophenyl)-6-methoxy-s-triazine-2,4(1H,3H)-dione, triethanolamine salt to increase the yield of rice plants by both foliar spray and soil application of this compound:

Rice seeds (cultivar, Starbonnet) were planted approximately 1.2 cm deep in Fallsington sandy loam soil contained in plastic pots 15 cm in diameter and then placed in the greenhouse. Eight days after planting, each pot was thinned to ten plants. 14 to 42 days after planting 3-(4-chlorophenyl)-6-methoxy-s-triazine-2,4(1H,3H)-dione, triethanolamine salt was applied at 0.5 kg/ha either as a foliar spray or soil application. Water was used as a solvent and foliar spray solutions contained 0.2% Tween 20 surfactant. Treatments were replicated four times. All treatments were harvested 173 days after planting. Results are presented in Table II below:

TABLE II

| Treatment | No. seeds per pot | % of Control | Seed wt. gm per pot | % of Control |
|---|---|---|---|---|
| 14 days (2 leaves) 0.5 kg/ha | | | | |
| soil application | 796 | 132 | 15.2 | 126 |
| foliar spray | 893 | 148 | 17.7 | 146 |
| 42 days (5 leaves) 0.5 kg/ha | | | | |
| soil application | 1172 | 194 | 23.0 | 190 |
| foliar spray | 1124 | 186 | 22.6 | 187 |
| Control | 603[a] | | 12.1[a] | |

[a]Averages of four controls each replicated four times.

Formulation of the Compounds

Useful formulations of the compounds of Formula I can be prepared in conventional ways. They include dusts, granules, pellets, solutions, suspensions, emulsions, wettable powders, emulsifiable concentrates, and the like. Many of these may be applied directly. Sprayable formulations can be extended in suitable media and used at spray volumes of from a few pints to several hundred gallons per acre. High strength compositions are primarily used as intermediates for further formulation. Many of the formulations can be applied as seed coatings, extended in a suitable media or used as dip solutions. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following proportions:

| | Percent by Weight | | |
|---|---|---|---|
| | Active Ingredient | Diluent(s) | Surfactant(s) |
| Wettable Powders | 20 – 90 | 0 – 74 | 1 – 10 |
| Oil Suspensions, Emulsions, Solutions (including Emulsifi- | 5 – 50 | 40 – 95 | 0 – 15 |

-continued

| able Concentrates | Percent by Weight | | |
|---|---|---|---|
| | Active Ingredient | Diluent(s) | Surfactant(s) |
| Aqueous Suspensions | 10 – 50 | 40 – 84 | 1 – 20 |
| Dusts | 1 – 25 | 70 – 99 | 0 – 5 |
| Granules and Pellets | 1 – 95 | 5 – 99 | 0 – 15 |
| High Strength Compositions | 90 – 99 | 0 – 10 | 0 – 2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Coloring agents can also be added. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, New York, 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19, and Examples 10 through 41.

R. W. Luckenbaugh, U.S. Pat. No. 3,309,192, Mar. 14, 1967, Col. 5, Line 43 through Col. 7, Line 62, and Ex. 8, 12, 15, 39, 41, 52, 53, 58, 132, 138–140, 162–164, 166, 167, 169–182

H. Gysin and E. Knusli, U.S. Pat. No. 2,891,855, June 23, 1959, Col. 3, Line 66 through Col. 5, Line 17, and Examples 1–4

G. C. Klingman, "Weed Control as a Science", John Wiley & Sons, Inc., New York, 1961, pp. 81–96

J. D. Fryer and S. A. Evans, "Weed Control Handbook", 5th Edn. Blackwell Scientific Publications, Oxford, 1968, pp. 101–103

Examples of suitable formulations of compounds used in the method of the present invention include the following:

EXAMPLE 6

Wettable Powder

| | |
|---|---|
| 3-(4-chlorophenyl)-6-methoxy-s-triazine-2,4(1H,3H)-dione | 40 % |
| dioctyl sodium sulfosuccinate | 1.5 % |
| sodium ligninsulfonate | 3 % |
| low viscosity methyl cellulose | 1.5 % |
| attapulgite | 54 % |

The ingredients are thoroughly blended, passed through an air mill, to produce an average particle size under 15 microns, reblended, and sifted through a U.S.S. No. 50 sieve (0.3 mm opening) before packaging.

EXAMPLE 7

High Strength Concentrate

| | |
|---|---|
| 3-(4-chlorophenyl)-6-methoxy-s-triazine-2,4(1H,3H)-dione, triethanol amine salt | 91 % |
| Sodium monohydrogen phosphate | 5 % |
| Alkanol × C | 1 % |
| HiSil 233 | 2 % |
| Sugar | 1 % |

The ingredients are thoroughly blended, passed through a hammer mill to produce a powder essentially all passing a U.S.S. No. 50 sieve (0.3 mm openings). This material is soluble in water.

EXAMPLE 8

Dust

| | |
|---|---|
| high strength concentrate (Example 7 above) | 28 % |
| pyrophyllite, powdered | 72 % |

The materials are thoroughly blended and packaged for use.

EXAMPLE 9

Aqueous Suspension

| | |
|---|---|
| 3-(4-bromophenyl)-6-methoxy-s-triazine-2,4(1H,3H)-dione | 25 % |
| hydrated attapulgite | 3 % |
| crude calcium ligninsulfonate | 10 % |
| sodium dihydrogen phosphate | 0.5 % |
| water | 61.5 % |

The ingredients are ground together in a ball or roller mill until the solid particles have been reduced to diameters under 10 microns.

EXAMPLE 10

Oil Suspension

| | |
|---|---|
| 3-(4-chlorophenyl)-6-methoxy-s-triazine-2,4(1H,3H)-dione | 25 % |
| polyoxyethylene sorbitol hexaleate | 5 % |

11
-continued

| highly aliphatic hydrocarbon oil | 70 % |
|---|---|

Grind the ingredients together in a sand mill until the solid particles have been reduced to under about 5 microns. The resulting thick suspension may be applied directly, but preferably after being extended with oils or emulsified in water.

EXAMPLE 11

Solution

| 3-(4-chlorophenyl)-6-methoxy-s-triazine-2,4(1H,3H)-dione, triethylamine salt | 25 % |
|---|---|
| dimethyl formamide | 75 % |

The ingredients are stirred together to produce a solution which can be applied as a low volume concentrate or diluted with water prior to application.

EXAMPLE 12

Granules

The solution of Example 11 (above) is sprayed onto preformed montmorillonoid clay granules (0.6–2.5 mm in diameter) tumbling in a rotating drum. The rate of spray is adjusted to produce a 5% active granule. These are then packaged and are ready for use.

EXAMPLE 13

Seed Treatment Wettable Powder

| 3-(4-chlorophenyl)-6-methoxy-s-triazine-2,4(1H,3H)-dione | 60.0 % |
|---|---|
| Polyfon H (sugar-free, sodium based sulfonates of Kraft lignin) | 4.0 % |
| Tergitol TMN (Trimethyl nonyl polyethylene glycol ether) | 4.0 % |
| diatomaceous earth | 27.0 % |
| Rhodamine B extra (dye) | 1.0 % |
| Sugar | 4.0 % |

The liquid Tergitol is thoroughly mixed with the diatomaceous earth to produce a uniform, dry mixture. The remaining ingredients are then added, blended, and ground in a hammer mill to produce a powder essentially all passing a U.S.S. No. 50 sieve (0.3 mm openings).

Seeds are coated using an aqueous slurry of this formulation.

EXAMPLE 14

Seed Pelleting Formulation

| 3-(4-bromophenyl)-6-methoxy-s-triazine-2,4(1H,3H)-dione | 1.0 % |
|---|---|
| Polyfon H (sugar-free, sodium-based sulfonates of Kraft lignin) | 0.5 % |
| Kaolinite clay | 98.5 % |

The ingredients are thoroughly blended and ground in a hammer mill to produce a powder essentially all passing a U.S.S. No. 50 sieve (0.3 mm opening).

Seeds and an appropriate amount of the above formulation, to yield from 30 to 3,000 gm of active per Kg. of seeds, are placed on a rotating pan granulator. As the seeds and formulation are tumbled on the granulator, enough water is sprayed onto the mixture to cause the powder to adhere to the seeds. The seeds are dried and are ready for use.

What is claimed is:

1. A method for increasing the yield of rice crops which comprises applying an effective amount of an s-triazinedione to rice seeds, seedlings, or to soil in which rice seeds or seedlings are planted, not later than 80 days after planting, the s-triazinedione being a compound of the formula

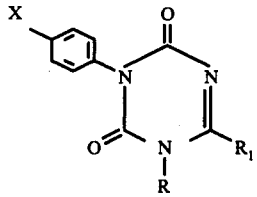

wherein
X is chlorine, bromine, or iodine;
R is hydrogen or a cation selected from lithium, sodium, potassium, calcium, magnesium, barium, or

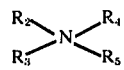

where
$R_2$, $R_3$, and $R_4$ can be the same or different and each can be hydrogen, alkyl of 1 through 4 carbon atoms, or hydroxy alkyl of 2 through 4 carbon atoms; and $R_5$ is hydrogen, alkyl of 1 through 12 carbon atoms, or benzyl; $R_2$ and $R_3$ can be taken together to form a ring that is $-(CH_2)_2-O-(CH_2)_2-$ or $-(CH_2)_n-$ where n is 4 through 6 and $R_4$ and $R_5$ are hydrogen; and
$R_1$ is $SR_6$ or $OR_6$ where $R_6$ is methyl or ethyl.

2. Method of claim 1 wherein the s-triazinedione is selected from the group consisting of 3-(4-chlorophenyl)-6-methoxy-s-triazine-2,4(1H,3H)-dione and salts thereof.

3. Method of claim 1 wherein the s-triazinedione is applied to the seed by seed soaking prior to seed planting.

4. Method of claim 3 wherein the s-triazinedione is applied to the seed by soaking for ¼ to 24 hours in a solution containing 1,000 to 15,000 ppm of the s-triazinedione.

5. Method of claim 3 wherein the s-triazinedione is applied to the seed by soaking ½ to 12 hours in a solution containing 4,000 to 10,000 ppm of the s-triazinedione.

6. Method of claim 3 wherein the s-triazinedione is applied to the seed by soaking 1 to 6 hours in a solution containing 4,000 to 10,000 ppm of the s-triazinedione.

7. Method of claim 1 wherein the s-triazinedione is applied to the seed by seed treatment prior to planting.

8. Method of claim 7 wherein said seed treatment is selected from the group consisting of seed coating and seed pelletization.

9. Method of claim 8 wherein the seeds are treated with 30 to 30,000 grams of s-triazinedione per 100 kg of seed.

10. Method of claim 8 wherein the seed is treated with 60 to 1,250 grams of s-triazinedione per 100 kg of seed.

11. Method of claim 8 wherein the seed is treated with 125 to 500 grams of s-triazinedione per 100 kg of seed.

12. Method of claim 1 wherein the s-triazinedione is applied to the rice seedlings by dipping prior to transplanting.

13. Method of claim 12 wherein the s-triazinedione is applied to the rice seedlings by dipping for ¼ to 24 hours in a solution containing 1,000 to 15,000 ppm of the s-triazinedione.

14. Method of claim 12 wherein the s-triazinedione is applied to the rice seedlings . by dipping for ½ to 12 hours in a solution containing 4,000 to 10,000 ppm of the s-triazinedione.

15. Method of claim 12 wherein the s-triazinedione is applied to the rice seedlings by dipping for 1 to 6 hours in a solution containing 4,000 to 10,000 ppm of the s-triazinedione.

16. Method of claim 1 wherein the s-triazinedione is applied to the seeds or seedlings by a technique selected from the group consisting of foliar spray and soil application.

17. Method of claim 16 wherein the s-triazinedione is applied to the seeds or seedlings at a rate of ¼ to 6 kg/Ha.

18. Method of claim 16 wherein the s-triazinedione is applied to the seeds or seedlings prior to 65 days after planting and at a rate of ½ to 4 kg/ha.

19. Method of claim 16 wherein the s-triazinedione is applied to the seeds or seedlings between 10 and 45 days after planting and at a rate of 1 to 3 kg/ha.

* * * * *